United States Patent [19]

Schwarz et al.

[11] 3,948,888

[45] Apr. 6, 1976

[54] PROCESS FOR REMOVING BORIC ACID FROM LACTAMS

[75] Inventors: Hans-Helmut Schwarz, Krefeld-Traar; Otto Immel, Krefeld, both of Germany

[73] Assignee: Bayer Aktiengesellschaft, Germany

[22] Filed: Jan. 7, 1974

[21] Appl. No.: 431,285

[30] Foreign Application Priority Data

Jan. 13, 1973 Germany............................ 2301587

[52] U.S. Cl..................... 260/239.3 A; 260/293.86
[51] Int. Cl.²................. C07D 201/16; C01B 35/10
[58] Field of Search................. 260/239.3 A, 293.86

[56] References Cited
UNITED STATES PATENTS

| | | | |
|---|---|---|---|
| 3,145,198 | 8/1964 | Morbidelli et al. | 260/239.3 A |
| 3,154,539 | 10/1964 | Irnich | 260/239.3 A |
| 3,418,314 | 12/1968 | Schwarz et al. | 260/239.3 A |
| 3,600,381 | 8/1971 | Yamamoto et al. | 260/239.3 A |

*Primary Examiner*—Henry R. Jiles
*Assistant Examiner*—Robert T. Bond
*Attorney, Agent, or Firm*—Connolly and Hutz

[57] ABSTRACT

The invention relates to a process for removing boric acid from a lactam which still contains boric acid and has been produced by catalytic rearrangement of oximes wherein an alkali and/or alkaline earth oxide and/or hydroxide is added to said lactam, the resulting mixture is filtered and the lactam is recovered from the filtrate. Not withstanding the high solubility of inorganic salts in lactams the boric acid can substantially be removed.

6 Claims, No Drawings

PROCESS FOR REMOVING BORIC ACID FROM LACTAMS

The catalytic re-arrangement of oximes into lactams in the gaseous phase is acquiring increasing commercial significance because, in this process, in contrast to the conventional Beckmann re-arrangement in sulphuric acid, no ammonium sulphate is formed as an undesirable secondary product. Re-arrangement in the gaseous phase is predominantly carried out using catalysts containing boric acid. The boric acid is volatile to some extent under the reaction conditions, with the result that the lactam formed is contaminated with boric acid.

When used as a starting material for plastics and fibres, the lactam monomer should be extremely pure. Accordingly, effective purifying operations are required to remove the boric acid and secondary products formed during the reaction from the lactam. It is obvious to separate lactam and boric acid by distillation. Unfortunately, distillation involves several difficulties owing to the fact that the boric acid acts as a polymerisation catalyst for lactam, both on account of the acidic properties of boric acid and on account of the temperatures required for carrying out distillation. In addition, some insoluble products are formed by the reaction of boric acid with lactam and other nitrogen-containing impurities which may be present. The condensation products formed adhere to and form crusts on the heat-exchange surfaces of the evaporators and, furthermore, cause lactam to be lost.

It is known that inorganic salts are highly soluble in lactams. An object of the invention was to develop a process for removing these highly soluble impurities from the lactams with as little outlay as possible.

Accordingly, the invention provides a process for removing boric acid from lactams, in which alkali and-/or alkaline earth oxides and/or hydroxides are added to lactams containing boric acid, optionally in the presence of organic solvents, followed by filtration.

In the process according to the invention, alkali and-/or alkaline earth hydroxide or oxide is added to the molten lactam or to lactam solutions in organic solvents in such a quantity that the molar ratio of base to boric acid is preferably in the range of from 0.5 : 1 to 3 : 1. The base can be added either in solid or in dissolved form. In cases where solid oxides or hydroxides are used, it is advisable to use them in finely powdered from. However, it is possible with equal effect to use solutions in water or alcohols such as methanol, ethanol, glycol or glycol ethers, providing they are thoroughly admixed with the lactam or the lactam solution. The duration of the treatment and the reaction temperature can fluctuate within wide limits. Favourable results are obtained at reaction temperatures of from 40° to 150°C, preferably from 40° to 125°C, with a reaction time of from 5 minutes to 2 hours, preferably from 10 to 60 minutes. Particularly favourable results are obtained by carrying out this treatment with organic solvents present in the reaction mixture in concentrations of from 5 to 80 % by weight.

The molar ratio of base to boric acid 0.5 : 1 to 3 : 1. For reasons of economy and by virtue of their better solubility, it is particularly preferred to use alkali hydroxides which show extremely high activity in a molar ratio of from 0.8 : 1 to 1.2 : 1.

On completion of the treatment, the reaction mixture is filtered, leaving a filtrate which is substantially free from boric acid. Filtration can be carried out by various methods and, hence, in any of the filtration apparatus commonly used in the art. It has proved to be advantageous in some cases to add filtration aids in order to obtain a high filtration rate.

The organic solvents which can be used in these processes in concentrations of from 5 to 80 % by weight, and preferably in concentrations of from 20 to 50 % by weight, based on the mixture as a whole, emanate from the following classes of substances: linear or branched aliphatic hydrocarbons containing 5 to 12 carbon atoms, such as pentane, hexane, heptane, octane, nonane, decane, undecane, dodecane, cyclohexane; aromatic hydrocarbons containing 6 to 10 carbon atoms such as benzene, toluene, xylenes, mesitylene, ethylbenzene; ethers such as dioxan, tetrahydrofuran; chlorinated aliphatic and aromatic hydrocarbons, such as methylene chloride, chloroform, chlorobenzene; ketones such as acetone cyclohexanone and mixtures thereof.

The following compounds are mentioned as examples of alkali and/or alkaline earth oxides and hydroxides that are active in accordance with the invention: lithium, potassium, sodium, magnesium and calcium hydroxide, calcium and barium oxide; it is preferred to use sodium, potassium, magnesium or calcium hydroxide, as well as calcium oxide. The process can be carried out either continuously or in batches.

The process is particularly intended for the removal of boric acid from caprolactam, although it can also be used for purifying lactams derived, for example, from ω-aminovaleric acid, ω-aminocaprylic acid, ω-aminoundecanoic acid or from ω-aminolauric acid.

The invention is illustrated by, but by no means limited to, the following Examples.

EXAMPLE 1

500 g batches of lactams containing boric acid are mixed with 2.5 ml of 18.6 % sodium hydroxide solution. The solvent is then added. The mixture is stirred for 30 minutes and then filtered, a Kieselguhr of the type known as Hyflo Super Cel [R], manufactured by Messrs. Johns-Manville, being used as filtration aid. The following Table shows the conditions and results of the tests.

| Solvent | ml | temp. | % boron in lactam before | after the reaction |
|---|---|---|---|---|
| chlorobenzene | 250 | 80 | 0.031 | 0.0063 |
| tetrahydrofuran | 250 | 80 | 0.025 | 0.012 |
| $CHCl_3$ | 250 | 80 | 0.024 | 0.013 |
| $CH_2Cl_2$ | 250 | 70 | 0.024 | 0.0075 |

EXAMPLE 2

300 g of crude lactam containing 1.15 % of $H_3BO_3$ are stirred with 50 g of toluene and 2.22 g of NaOH for 3 hours at 148°C and subsequently filtered. The filtrate has a boron content of 20 ppm.

EXAMPLE 3

306 g of caprolactam containing 3 % of boric acid and 2 % of cyclohexanol are mixed at 85°C with 5.85 g of powdered sodium hydroxide, intensively stirred for 0.75 hour and subsequently filtered. The filtrate has a boric acid content of 0.0012 %.

EXAMPLE 4

Alkali or alkaline earth oxide/hydroxide is added in various quantities to 50 g batches of a solution of 200 g of caprolactam, 200 g of cyclohexanone oxime and 30 g of boric acid in 600 g of toluene (boron content 0.5 %), stirred for 2 hours and filtered. The boron content is determined from the filtrate. The results of these tests are set out in the following Table:

| Quantity of base added | Boron content of the solution after filtration (%) |
|---|---|
| 3.93 g of KOH | 0.0082 |
| 1.31 g of KOH | 0.0030 |
| 0.29 g of CaO | 0.35 |
| 0.9 g of Mg(OH)$_2$ | 0.33 |
| 1.86 g of NaOH | 0.0062 |

EXAMPLE 5

300g of caprolactam containing 3 % of boric acid are mixed at 90°C with a solution of 5.85 g of NaOH in 6 g of water and stirred for 30 minutes. After filtration, the solution contains less than 0.001 % of boron.

EXAMPLE 6

50 g of lactam containing 0.02 % of boron are dissolved in 150 g of toluene. 1 ml of n/1 NaOH is added with stirring at 125°C. After 30 minutes, the mixture is filtered using Hydro Super Cel$^{(R)}$ as filtration aid. The filtrate has a boron content of less than 10 ppm.

We claim:

1. A process for removing boric acid from a lactam which comprises mixing at least one member selected from the group consisting of oxides and hydroxides of alkali metal and alkaline earth metal oxides with the boric acid containing lactam in a molar ratio amount of selected member to boric acid of from 0.5:1 to 3:1, maintaining the reaction temperature of said mixture at from 40° to 150°C. for from 5 minutes to 2 hours and then filtering resulting reaction mixture.

2. The process of claim 1 which is carried out in the presence of from 5 to 80% by weight, based on the weight of said mixture, of an organic solvent.

3. The process of claim 1 wherein said lactam is caprolactam.

4. The process of claim 1 wherein said selected member is selected from the group consisting of sodium hydroxide, potassium hydroxide, magnesium hydroxide and calcium oxide.

5. The process of claim 1 wherein said molar ratio is from 0.8:1 to 1.2:1.

6. The process of claim 1 which is carried out continuously.

* * * * *